US00PP20568P2

(12) United States Plant Patent
Bronsther

(10) Patent No.: US PP20,568 P2
(45) Date of Patent: Dec. 15, 2009

(54) ***ABELIA* PLANT NAMED 'RIKA 1'**

(50) Latin Name: *Abelia×grandiflora*
Varietal Denomination: Rika 1

(76) Inventor: Rika Bronsther, 37 St. Paul's Pl., Hempstead, NY (US) 11550

( * ) Notice: Subject to any disclaimer, the term of this patent is extended or adjusted under 35 U.S.C. 154(b) by 0 days.

(21) Appl. No.: 12/284,882

(22) Filed: Sep. 22, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent L Bell
(74) *Attorney, Agent, or Firm*—C. A. Whealy

(57) ABSTRACT

A new and distinct cultivar of *Abelia* plant named 'Rika 1', characterized by its upright and somewhat outwardly spreading plant habit; freely branching habit; dense and bushy growth habit; leaves that are initially copper-bronze in color becoming yellow green or green in color with development; white-colored flowers; and good garden performance.

2 Drawing Sheets

Botanical designation: *Abelia×grandiflora.*
Cultivar denomination: 'Rika 1'.

BACKGROUND OF THE INVENTION

The present invention relates to a new and distinct cultivar of *Abelia,* botanically known as *Abelia×grandiflora* and hereinafter referred to by the name 'Rika 1'.

The new *Abelia* is a naturally-occurring branch mutation of an unnamed selection of *Abelia×grandiflora,* not patented. The new *Abelia* was discovered and selected by the Inventor in June, 2003 in a controlled outdoor nursery environment in Hempstead, N.Y.

Asexual reproduction of the new *Abelia* plant by softwood cuttings in a controlled greenhouse environment in Grand Haven, Mich. since May, 2004 has shown that the unique features of this new *Abelia* plant are stable and reproduced true to type in successive generations of asexual reproduction.

SUMMARY OF THE INVENTION

Plants of the new *Abelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Rika 1'. These characteristics in combination distinguish 'Rika 1' as a new and distinct cultivar of *Abelia:*

1. Upright and somewhat outwardly spreading plant habit.
2. Freely branching habit; dense and bushy growth habit.
3. Leaves that are initially copper-bronze in color becoming yellow green or green in color with development.
4. White-colored flowers.
5. Good garden performance.

Plants of the new *Abelia* can be compared to plants of the parent selection. Plants of the new *Abelia* differ from plants of the parent selection in the following characteristics:

1. Developing leaves of plants of the new *Abelia* are copper-bronze in color whereas developing leaves of plants of the parent selection are faintly copper-bronze in color.

2. Fully developed leaves of plants of the new *Abelia* are yellow green or green in color whereas fully developed leaves of plants of the parent selection are green in color.

Plants of the new *Abelia* can be compared to plants of the *Abelia×grandiflora* 'Minipan', not patented. In side-by-side comparisons conducted in Grand Haven, Mich., plants of the new *Abelia* differed from plants of 'Minipan' in the following characteristics:

1. Plants of the new *Abelia* were more vigorous than plants of 'Minipan'.
2. Developing leaves of plants of the new *Abelia* were copper bronze in color whereas developing leaves of plants of 'Minipan' were yellow gold in color.
3. Fully developed leaves of plants of the new *Abelia* were yellow green or green in color whereas fully developed leaves of plants of 'Minipan' were green and gold in color.
4. Plants of the new *Abelia* were more freely flowering than plants of 'Minipan'.

Plants of the new *Abelia* can also be compared to plants of the *Abelia×grandiflora* 'Francis Mason', not patented. In side-by-side comparisons conducted in Grand Haven, Mich., plants of the new *Abelia* differed from plants of 'Francis Mason' in the following characteristics:

1. Developing leaves of plants of the new *Abelia* were copper bronze in color whereas developing leaves of plants of 'Francis Mason' were slightly copper bronze in color.
2. Fully developed leaves of plants of the new *Abelia* were yellow green or green in color whereas fully developed leaves of plants of 'Francis Mason' were yellow green and gold in color; leaf color of plants of 'Francis Mason' becoming green in color with development.

BRIEF DESCRIPTION OF THE PHOTOGRAPHS

The accompanying colored photographs illustrate the overall appearance of the new *Abelia,* showing the colors as true as it is reasonably possible to obtain in colored reproductions of this type. Colors in the photographs may differ slightly from the color values cited in the detailed botanical description which accurately describe the colors of the new *Abelia.*

The photograph at the bottom of the first sheet is a side perspective view of a typical plant of 'Rika 1' grown in an outdoor nursery.

The photograph at the top of the first sheet is a close-up view of typical leaves of 'Rika 1'.

The photograph on the second sheet is a close-up view of typical flower buds and flowers of 'Rika 1'.

DETAILED BOTANICAL DESCRIPTION

The aforementioned photographs and following observations, measurements and values describe plants grown in Grand Haven, Mich. during the spring and summer in an outdoor nursery and under conditions which closely approximate commercial production. Plants had been growing for four years when the photographs and the description were taken. In the description, color references are made to The Royal Horticultural Society Colour Chart, 1995 Edition, except where general terms of ordinary dictionary significance are used.

Botanical classification: *Abelia×grandiflora* 'Rika 1'.

Parentage: Naturally-occurring branch mutation of an unnamed selection of *Abelia×grandiflora,* not patented.

Propagation:

*Type.*—By softwood cuttings.

*Time to initiate roots.*—About 20 days at 24° C.

*Time to produce a rooted young plant.*—About three months at 24° C.

*Root description.*—Fine.

*Rooting habit.*—Freely branching; dense.

Plant description:

*Plant form and growth habit.*—Perennial shrub. Upright and somewhat outwardly spreading plant habit. Vigorous growth habit.

*Branching habit.*—Freely branching habit, dense and bushy growth habit, usually about 18 lateral branches develop per plant.

*Plant height.*—About 31 cm.

*Plant diameter* (*area of spread*).—About 54 cm.

Lateral branch description:

*Length.*—About 23 cm.

*Diameter.*—About 2.5 mm.

*Internode length.*—About 3 cm to 5 cm.

*Aspect.*—About 35° to 40° from vertical.

*Texture.*—Slightly pubescent.

*Color, immature.*—Close to 46A.

*Color, mature.*—Close to 199B.

Foliage description:

*Arrangement.*—Opposite, simple.

*Length.*—About 3.2 cm.

*Width.*—About 1.7 cm.

*Shape.*—Ovate.

*Apex.*—Acute.

*Base.*—Obtuse.

*Margin.*—Slightly crenate.

*Texture, upper and lower surfaces.*—Smooth, glabrous.

*Venation pattern.*—Pinnate.

Color.—Developing leaves, upper surface: Close to 164A. Developing leaves, lower surface: Between 164A and 151A. Fully expanded leaves, upper surface: Close to 151A or 137A; venation, similar to leaf surface color. Fully expanded leaves, lower surface: Close to 151A or 137D; venation, similar to leaf surface color.

*Petiole.*—Length: About 4 mm. Diameter: About 1.5 mm. Texture, upper and lower surfaces: Smooth, glabrous. Color, upper and lower surfaces: Close to 46B.

Flower description:

*Flower appearance/arrangement.*—Single campanulate flowers; solitary or in clusters; terminal and axillary. Freely flowering habit with 64 to 192 flowers developing per lateral branch. Flowers face upright to outwardly.

*Fragrance.*—Slight, pleasant.

*Flower longevity.*—Flowers last for about three to seven days on the plant. Flowers not persistent.

*Natural flowering season.*—Long flowering period, plants typically flower from June to September in Michigan.

*Flower diameter.*—About 1.8 cm.

*Flower depth.*—About 2.8 cm.

*Flower bud.*—Length: About 1 cm. Diameter: About 3 mm. Shape: Obovate. Color: Close to 145A tinged with close to 46A.

*Petals.*—Arrangement/quantity: Single whorl of five fused petals. Lobe length: About 7 mm. Lobe width: About 5 mm. Shape: Oblong. Apex: Obtuse. Margin: Entire. Texture, upper surface: Slightly pubescent. Texture, lower surface: Smooth, glabrous. Color: When opening and fully opened, upper surface: Close to 155D. When opening and fully opened, lower surface: Close to 155D.

*Sepals.*—Quantity/arrangement: About four to five in a single whorl. Length: About 8 mm. Width: About 3 mm. Shape: Narrowly elliptic. Apex: Acute to obtuse. Base: Cuneate. Margin: Entire. Texture, upper and lower surfaces: Smooth, glabrous. Color, immature, upper and lower surfaces: Close to 145C. Color, mature, upper and lower surfaces: Close to 52A to 52B.

*Peduncles.*—Length: About 3 mm. Diameter: About 1 mm. Strength: Strong, flexible. Texture: Smooth, glabrous. Angle: About 10° from the stem axis. Color: Close to 46A.

*Reproductive organs.*—Stamens: Quantity per flower: About four. Anther length: About 2 mm. Anther color: Close to 155D. Pollen amount: Scarce. Pollen color: Close to 155B. Pistils: Pistil length: About 2 cm. Stigma shape: Round. Stigma color: Close to 155D. Style length: About 1.4 cm. Style color: Close to 155D.

*Seeds/fruits.*—Seed and fruit development have not been observed on plants of the new *Abelia* plant.

Garden performance: Plants of the new *Abelia* have been observed to have excellent garden performance and to tolerate rain, wind and temperatures ranging from about −20° C. to about 37° C.

Pathogen/pest resistance: Plants of the new *Abelia* have not been shown to be resistant to pathogens and pests common to *Abelia.*

It is claimed:

1. A new and distinct *Abelia* plant named 'Rika 1' as illustrated and described.

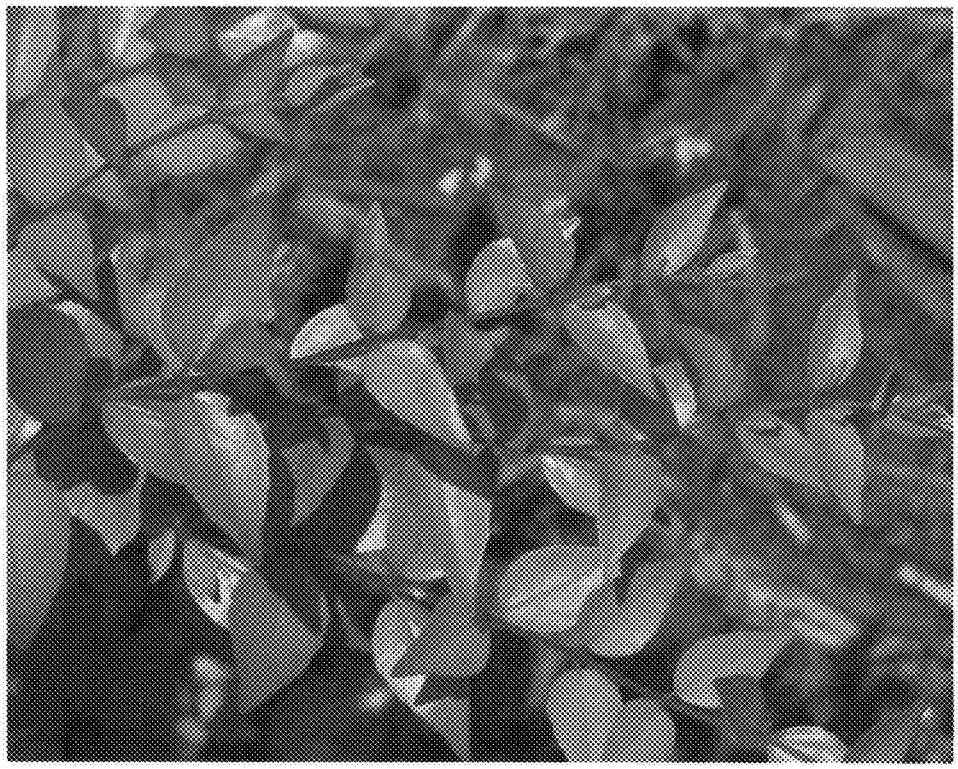
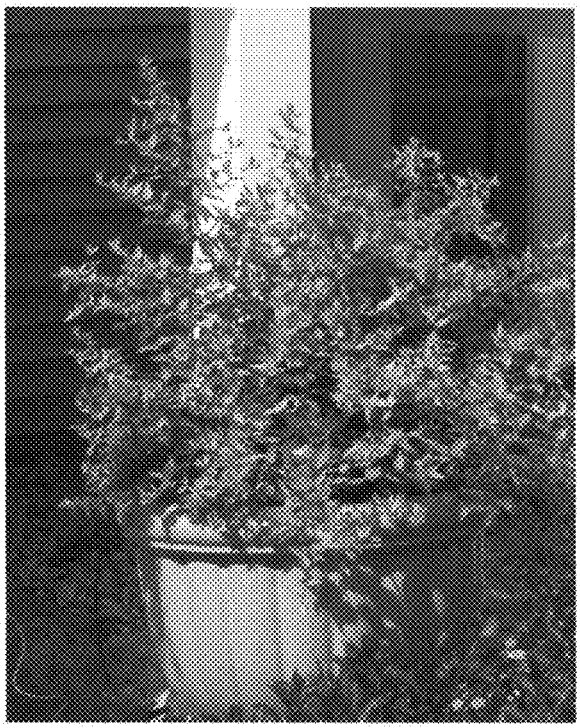

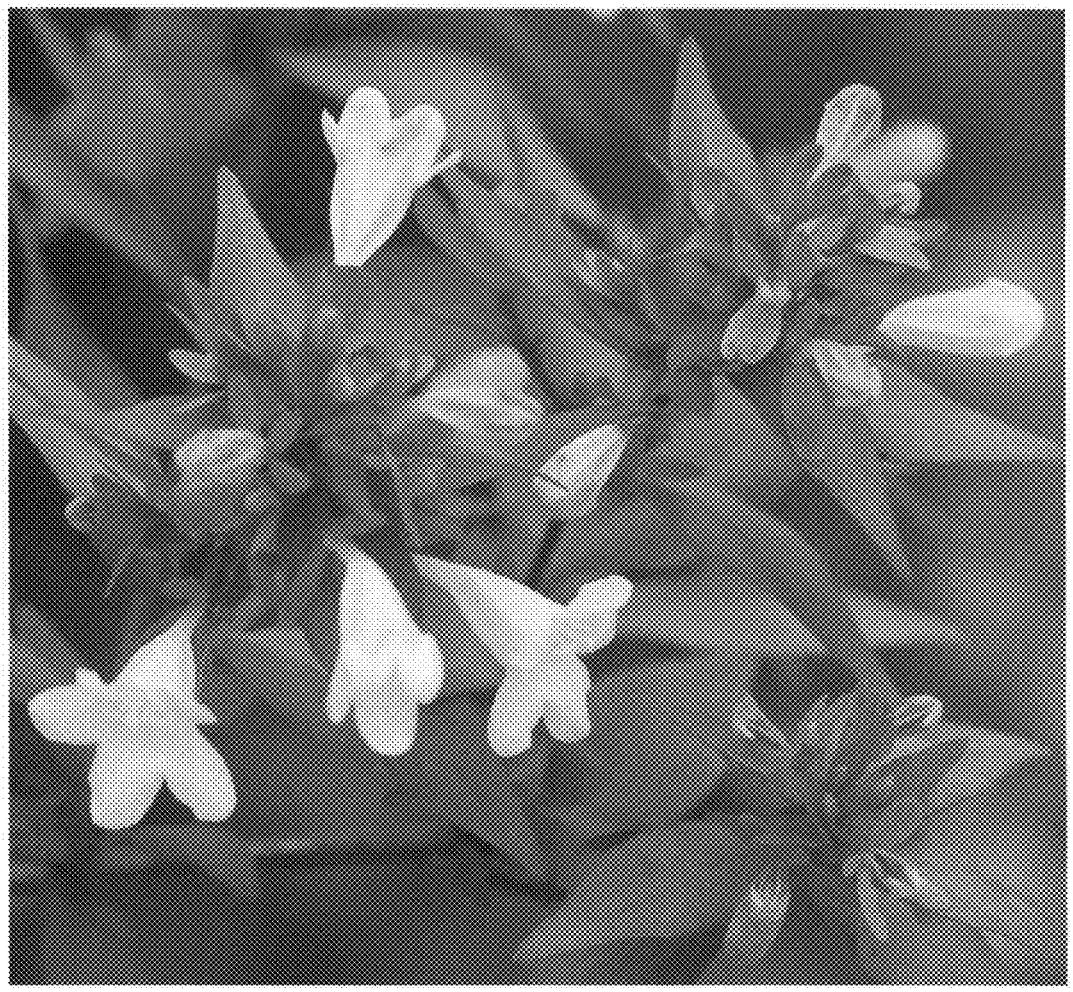

* * * * *